United States Patent [19]

Sun

[11] Patent Number: 5,206,250
[45] Date of Patent: Apr. 27, 1993

[54] BIS-NAPHTHALIMIDES CONTAINING AMIDE AND THIOAMIDE LINKERS AS ANTICANCER AGENTS

[75] Inventor: Jung-Hui Sun, Hockessin, Del.

[73] Assignee: Du Pont Merck Pharmaceutical Company, Wilmington, Del.

[21] Appl. No.: 676,062

[22] Filed: Mar. 27, 1991

[51] Int. Cl.$^5$ .................. C07D 471/06; A61K 31/44
[52] U.S. Cl. ..................................... 514/296; 546/99
[58] Field of Search ..................... 514/296; 546/99, 79

[56] References Cited

U.S. PATENT DOCUMENTS

| | | | |
|---|---|---|---|
| 4,841,052 | 6/1989 | Harnisch et al. | 544/361 |
| 4,874,863 | 10/1989 | Brana et al. | 540/99 |
| 5,086,059 | 2/1992 | Ardecky et al. | 514/284 |

*Primary Examiner*—Alan L. Rotman
*Attorney, Agent, or Firm*—Gerald J. Boudreaux

[57] ABSTRACT

There are provided novel bis-naphthalimide compounds useful as antitumor agents, pharmaceutical compositions containing them and processes for preparing such compounds.

8 Claims, No Drawings

BIS-NAPHTHALIMIDES CONTAINING AMIDE AND THIOAMIDE LINKERS AS ANTICANCER AGENTS

BACKGROUND OF THE INVENTION

1. Field of the Invention

This invention relates to bis-naphthalimides, processes for their preparation, pharmaceutical compositions containing them, and methods of using them to treat cancer in mammals.

2. Prior Art

Harnisch, et al. in U.S. Pat. No. 4,841,052 issued Jun. 20, 1989 describe naphthalic acid imides of the formula

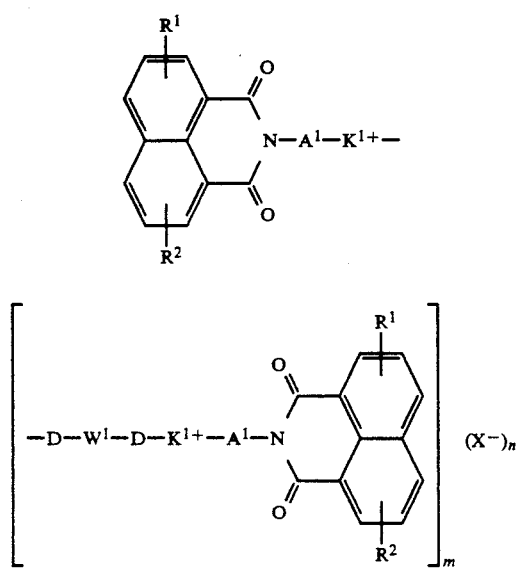

wherein:
$A^1$ represents $C_2-C_5$-alkylene,
$K^{1+}$ represents

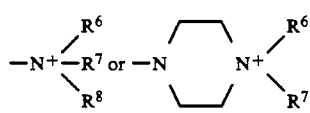

$R^6$ represents $C_1-C_{16}$-alkyl, carbamoylmethyl or benzyl;
$R^7$ represents methyl or ethyl or a single bond linked to D;
$R^8$ represents methyl or ethyl;
$W^1$ represents

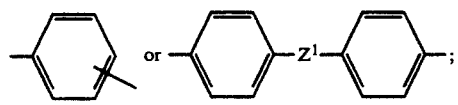

$Z^1$ represents —$CH_2$—, or

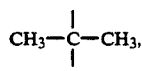

—O— or —$SO_2$—; and

X represents an unsubstituted benzosulphonate or a benzenesulphonate substituted by chlorine or $C_1-C_{12}$ alkyl, a $C_5-C_{18}$ alkylsulphonate or a salt of a $C_5-C_{18}$ alkylcarboxylic acid or a salt of a condensation product of formaldehyde and arylsulphonic acids and/or optionally sulphonated 4,4'-dihydroxy-diphenylsulphone, wherein D represents —$CH_2$—, —$CH_2$—CO—, —$CH_2$—CO—HN— or —$CH_2$—CO—NH—$CH_2$— and m represents 0 or 1.

These compounds are highly suitable as charregulating substances in electrophotographic toners.

U.S. Pat. No. 4,874,863 issued Oct. 17, 1989 discloses anticancer compounds of the formula

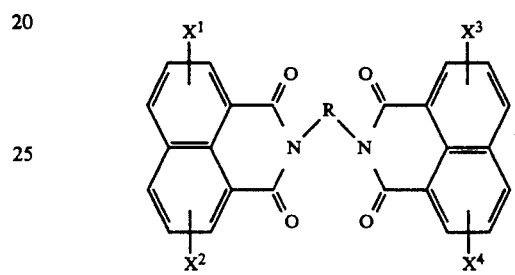

wherein $X^1$, $X^2$, $X^3$ and $X^4$ are identical or different and are each H, $NO_2$, $NH_2$, $C_1-C_6$-alkylamino, di-$C_1-C_6$-alkylamino, OH, $C_1-C_6$-alkoxy, halogen, trihalomethyl, $C_1-C_6$alkyl, formyl, $C_1-C_6$-alkylcarbonyl, ureyl, $C_1-C_6$-alkylureyl and R is a straight chain or branched $C_4-C_{10}$-alkylene which is interrupted at one or two points in the chain by a secondary or tertiary amino group, where 2 nitrogen atoms may additionally be bonded to one another by an alkylene group, or a salt with a physiologically tolerated acid.

SUMMARY OF THE INVENTION

This invention relates to bis-naphthalimide compounds having the Formula (i), pharmaceutical compositions containing these compounds and methods of using these compounds for treating cancer in a mammal. Also provided are processes for making such compounds.

A compound of the formula:

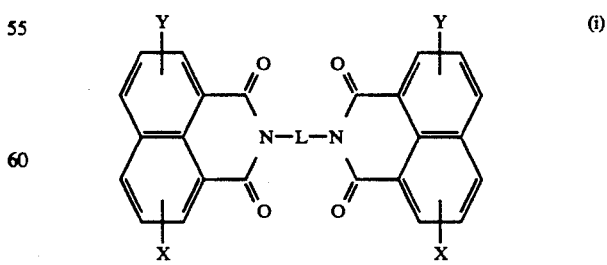

or a diastereomerically pure or a mixture of racemic and meso pharmaceutically acceptable salts thereof, wherein:

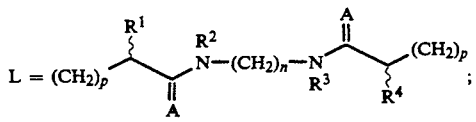

each $R^1$ and $R^4$ independently are H or $CH(X^2)(CH_2)_mX^3$;

$R^2$ and $R^3$ independently are H, $C_1$–$C_6$ alkyl; each A independently is O or S;

$X^2$ and $X^3$ independently are H, $CH_3$, phenyl, $OR^5$, $SR^6$, $N(R^7)_2$, 4-hydroxyphenyl, imidazoyl or indolyl;

X and Y independently are H, $NO_2$, halogen, $NHCOCF_3$, $NHSO_2CF_3$, $SO_2R^8$ or $N(R^9)_2$;

$R^5$, $R^6$, $R^8$ and $R^9$ independently are H, $C_1$–$C_6$ alkyl; each p independently is 0–4;

m is 0–4;

n is 0, 2–12; and $R^7$ is H or $C_1$–$C_6$ alkyl, provided that each $R^7$ in $N(R^7)_2$ cannot both be H.

Preferred compounds of the present invention are those compounds of Formula (i) wherein:

X is H or $NO_2$; and/or

Y is H or $NO_2$, provided that one of X or Y is $NO_2$; and/or n is 2–4; and/or p is 0; and/or A is O; and/or $R^1$ and $R^4$ are $CH_3$; and/or $R^2$ and $R^3$ are H.

Specifically preferred compounds of the present invention are:

a) The compound of claim 1 which is (S,S)-N,N'-1,2-ethanediylbis[α-methyl-5-nitro-1,3-dioxo-1H-benz[de]isoquinoline-2(3H)-acetamide].

b) The compound of claim 1 which is (R,R)-N,N'-1,2ethanediylbis[α-methyl-5-nitro-1,3-dioxo-1H-benz[de]isoquinoline-2(3H)-acetamide].

c) The compound of claim 1 which is (S,S)-N,N'-1,2ethanediylbis[α-methylthioethyl-5-nitro-1,3 dioxo-1H-benz[de]isoquinoline-2(3H)-acetamide.

d) The compound of claim 1 which is (S,S)-N,N'-1,4-butanediylbis[α-methyl-5-nitro-1,3-dioxo-1H-benz[de]isoquinoline-2(3H)-acetamide.

e) The compound of claim 1 which is (S,S)-N,N'-1,3propanediylbis[α-methyl-5-nitro-1,3-dioxo-1H-benz[de]isoquinoline-2(3H)-acetamide.

f) The compound of claim 1 which is (S,S)-N,N'-1,2ethanediylbis[α-methyl-5-nitro-1,3-dioxo-1H-benz[de] isoquinoline-2(3H)-ethanethioamide].

Synthesis

The present invention describes a series of bis-naphthalimides useful for treating cancer containing linkers derived from amino acids.

Compounds of this invention can be synthesized by reacting two equivalents of an anhydride of Formula (ii) with one equivalent of a polyamine of Formula (iii) in an inert solvent such as ethanol or dimethylformamide or tetrahydrofuran at a temperature ranging from ambient to the solvent's boiling temperature (Scheme A). The resulting suspension can then be filtered to give the free base of (iv) or it can be acidified with the appropriate mineral or organic acid to produce a pharmaceutically acceptable salt, which can be obtained by filtration.

Scheme A

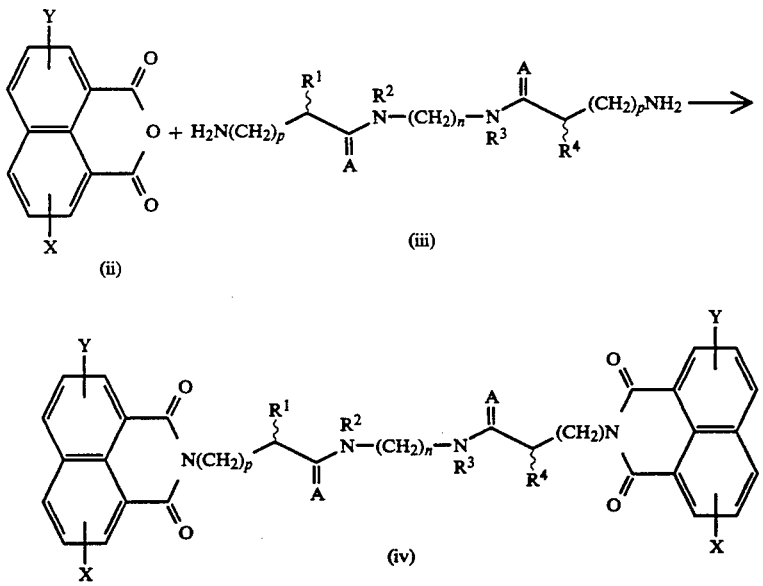

The parent anhydride (ii) is commercially available or can be prepared according to the procedures described by Hodgson et al, *J. Chem. Soc.*, p90 (1945. Amino acids of formula (iii) can be prepared according to the methods described below (Schemes I - II).

For compounds of formula (i) where A=O (Scheme I), the requisite amine IIa can be used for the synthesis of bis-naphthalimides. Ia is synthesized by the reaction of t-BOC-(S)-alanine with 1,1'-carbonyldiimidazole, followed by reaction with ethylenediamine under standard conditions. Acid hydrolysis of the t-BOC (N-tert-butoxycarbonyl) of Ia was performed under standard conditions to afford IIa. The same procedure is utilized to produce compounds IIb or IIc by starting the sequence with the corresponding (R)-aminoacid (b) or racemic amino acid (c).

Condensation of IIa (1.0 eq.) with the appropriate naphthalic anhydride (2.10 eq.) in ethanol containing triethylamine at reflux temperature afforded bisnaphthalimides of the formula (IIIa).

The invention can be further understood by referring to the following examples wherein parts and percentages are by weight unless otherwise specified.

EXAMPLE 1

Part A: Ia Bis (1,1'-dimethylethyl)

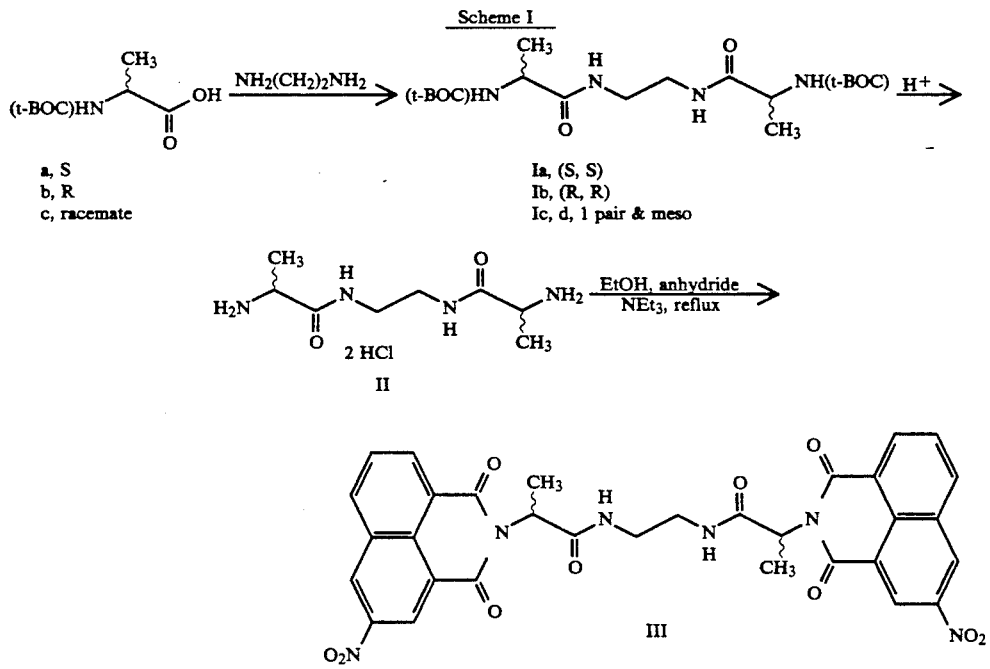

For compounds where A=S (Va, Scheme II), Ia is reacted with phosphorus pentasulfide in tetrahydrofuran at room temperature, followed by acid hydrolysis of the t-BOC protecting group. The resulting IVa is reacted with the appropriate naphthalic anhydride in ethanol contining triethylamine at reflux temperature to yield Va. Vb (R,R) and Vc (d, 1 pair+meso) could be prepared similarly by using the corresponding (R)-amino acid or racemate, respectively.

(S,S)-[1,2-ethanediylbis[imino(1-methyl)-2-oxo-2,1-ethanediyl)]] bis(carbamate)

A methylene chloride (700 ml) solution of N-t-BOC-(S)-alanine (37.84 g, 200 mmol) and 1,1'-carbonyldiimidazole (34.05 g, 210 mmol) were stirred with ice bath cooling for 2 hours. To this, there was added 6.69 ml (100 mmol) of ethylenediamine dropwise at 5° C. The mixture was then stirred at ambient temperature overnight. The solution was washed with saturated

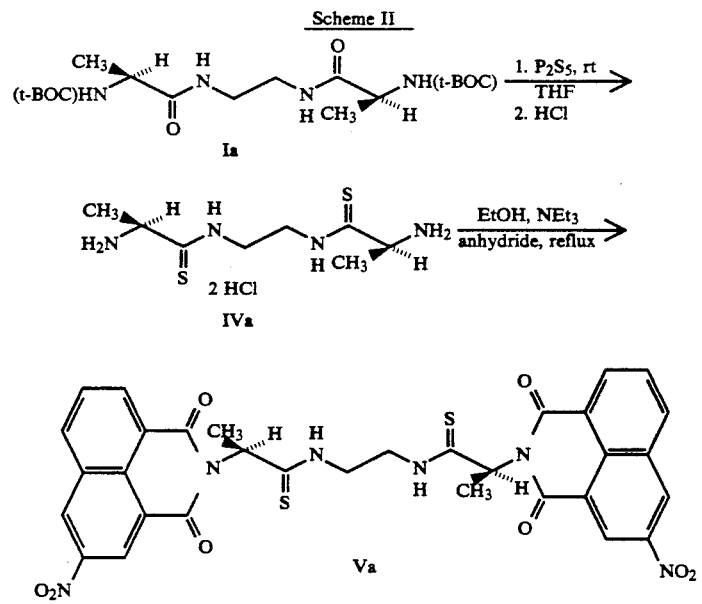

Na$_2$CO$_3$ (2×100 ml), brine (133 200 ml), dried over anhydrous MgSO$_4$, filtered and evaporated to give 39.22 g (97.4%) of Ia as a white solid, mp 150°-153° C. $^1$H-NMR (CDCl$_3$)δ 6.98 (broad, 2H, 2 NH), 5.28 (D, 2H, J=7.3 Hz, 2 NH), 4.13 (m, 2H, 2 CH) 3.49 (m, 2H), 3.30 (m, 2H), 1.44 (s, 18H, 6 CH$_3$) and 1.35 (d, 6H, J=7.3 Hz, 2 CH$_3$). IR (KBr) 1704, 1654 (C=0) cm$^{-1}$. MS (DCI) m/e 403 (M+1). [α]$_D$+19.43° (c=0.602, CHCl$_3$).

Part B: IIa
(S,S)-N,N'-1,2ethanediylbis[2-aminopropanamide] dihydrochloride

A mixture of Ia (12.07 g, 30 mmol) in 60 ml of 2.4 N HCl in dioxane was stirred at room temperature for 2 hours. The solvent in the reaction mixture was partially removed by rotatory evaporator, and the remaining mixture was treated with ethyl ether. The white solid was collected on a filter to give 7.1 g (86%) of IIa, which is very hygroscopic. $^1$H-NMR (D$_2$O) δ 3.87 (q, 2H, J=7.0 Hz, 2 CH), 3.21 (m, 4H, 2 CH$_2$) and 1.32 (d, 6H, J=7.4 Hz, 2 CH$_3$). MS (DCI) m/e 203 (M+1).

Part C: IIIa
(S,S)-N,N'-1,2-ethanediylbis[α-methyl-5-nitro-1, 3-dioxo-1H-benz[de]isoquinoline-2(3H)-acetamide]

A mixture of 3-nitro-1,8-naphthalic anhydride (4 86 g, 20 mmol), IIa (3.03 g, 11 mmol) and triethylamine (3.07 ml, 22 mmol) in 100 ml of ethanol was stirred at room temperature overnight and then refluxed for 4hours. The product was collected by filtration and then purified by heating in 250 ml of ethanol for 2 hours to give IIIa (4.83 g, 74%); mp 301°-304° C. (dec.). $^1$H-NMR (DMSO-d$_6$) δ 9.50 (broad s, 2H, aromatic protons), 8.94 (m, 2H, aromatic protons), 8.80 (d, 2H, J=7.0 Hz, aromatic protons), 8.66 (d, 2H, J=7.3 Hz, aromatic proatons), 8.07 (m, 2H, aromatic protons), 7.94 (broad s, 2H, 2 NH), 5.46 (m, 2H, 2 CH), 3.03 (broad s, 4H, 2 CH2) and 1.47 (d, 6H, J=6.6 Hz, 2 CH$_3$). MS (DCI) m/e 653 (M+1). [α]$_D$−56.90° (c=0.608, DMF). Anal. Calcd for C$_{32}$H$_{24}$N$_6$O$_{10}$·2H$_2$O (MW 688.61): C,55.82; H,4.10; N,12.20. Found: C,55.97, 55.83; H,3.70, 3.68; N,12.28, 12.16.

EXAMPLE 2
(R,R)-N,N'-1,2-ethanediylbis[α-methyl-5-nitro-1,3-dioxo-1H-benz[de]isoquinoline-2(3H)-acetamide]

Yield (72%); mp 293-294° C. (dec.). $^1$H-NMR (DMSO-d$_6$) δ9.50 (d, 2H, J=2.2 Hz, aromaticprotons), 8.94 (d, 2H, J=2.2 Hz, aromatic protons), 8.80 (d, 2H, J=8.1 Hz, aromatic protons), 8.66 (d, 2H, J=7.4 Hz, aromatic protons), 8.07 (t, 2H, J=7.9 Hz, aromatic protons), 5.45 (q, 2H, J=6.9 Hz, 2 CH), 3.03 (broad, 4H, 2 CH2) and 1.48 (d, 6H, J=7.0 Hz, 2 CH3). IR (KBr) 1711, 1670 (C=0)cm$^{-1}$ MS (DCI) m/e 653 (M+1). [α]$_D$+48.34° (c=0.606, DMF). Anal. Calcd for C$_{32}$H$_{24}$N$_6$O$_{10}$·H$_2$O (MW 670.59): C, 57.32; H, 3.91; N, 12.53. Found: C, 57.49, 57.51; H, 3.86, 3.59; N, 12.70, 12.76.

EXAMPLE 3
(S,S)-N,N'-1,2-ethanediylbis[α-methylthioethyl-5-nitro-1,3 dioxo-1H-benz[de]isoquinoline-2(3H)-acetamide Yield (61%); mp 232°-235° C. $^1$H-NMR (DMSO-d$_6$) δ 9.49 (d, 2H, J=2.0 Hz, aromatic protons), 8.92 (d, 2H, J=2.3 Hz, aromatic protons), 8.79 (d, 2H, J=7.9 Hz, aromatic protons), 8.65 (d, 2H, J=7.5 Hz, aromatic protons), 8.04 (t, 2H, J=7.9 Hz, aromatic protons), 7.91 (t, 2H, J=4.7 Hz, 2 NH), 5.48 (m, 2H, 2 CH), 2.96 (m, 4H, 2 CH$_2$N), 2.50 (m, 4H, 2 CH$_2$), 2.49 (m, 4H, 2 CH$_2$), 1.96(s, 6H, 2 CH$_3$) and 1.40 (m, 2H, CH$_2$). MS (DCI) m/e 787 (M+1).

EXAMPLE 4
(S,S)-N,N'-1,4-butanediylbis[α-methyl 5-nitro-1,3-dioxo-1H-benz[de]isoquinoline-2(3H)-acetamide Yellow solid (41%); mp 285°-288° C. (dec). $^1$H-NMR (DMSO-d$_6$) δ 9.49 (d, 2H, J=2.2 Hz, aromatic protons), 8.93 (d, 2H, J=2.2 Hz, aromatic protons), 8.79 (d, 2H, J=8.0 Hz, aromatic protons), 8.66 (d, 2H, J=6.9 Hz, aromatic protons), 8.06 (t, 2H, J=7.8 Hz, aromatic protons), 7.87 (broad, 2H, 2 NH), 5.42 (q, 2H, J=7.1 Hz, 2 CH), 3.0 (broad, 4H, 2 CH$_2$N), 1.49 (d, 6H, J=7.1 Hz, 2 CH$_3$) and 1.28 (broad s, 4H, 2 CH$_2$). MS (DCI) m/e 681 (M+1).

EXAMPLE 5
(S,S)-N,N'-1,3-propanediylbis[α-methyl-5-nitro-1,3-dioxo-1H-benz[de]isoquinoline-2(3H)-acetamide 48.9% yield; mp 255°-257° C. (dec.). $^1$H-NMR (DMSO-d$_6$) δ 9.47 (d, 2H, J=2.0 Hz, aromatic protons), 8.90 (d, 2H, aromatic protons), 8.76 (d, 2H, J=8.3 Hz, aromatic protons), 8.62 (d, 2H, J=7.3 Hz, aromatic protons), 8.03 (t, 2H, J=7.8 Hz, aromatic protons), 7.86 (t, 2H, J=5.4 Hz, aromatic protons), 5.40 (q, 2H, J=6.9 Hz, 2 CH), 3.00 (m, 4H, 2 CH$_2$N) and 1.45 (d, 8H, J=6.8 Hz, 2 CH$_3$ and CH$_2$). MS (DCI) m/e 667 (M+1).

EXAMPLE 6

Part A: IVa
(S,S)-N,N'-1,2-ethanediylbis[2-aminopropanethioamide] dihydrochloride A mixture of Ia (2.82 g, 7.0 mmol) and phosphorus pentasulfide (6.22 g, 28.0 mmol) in 70 ml of THF was stirred at room temperature for 3 days. The white solid was removed by filtration; and the filtrate treated with 4 ml of 4.8 N HCl in dioxane. After stirring for several hours, the solvent was evaporated. The residue was triturated with ethyl ether, filtered under nitrogen to give 1.5 g of a gummy solid, IVa (91%). $^1$H-NMR (DMSOd$_6$) δ 8.39 (broad s, 6H), 4.31 (m, 2H, 2 CH), 3.85 (s, 4H, 2 CH$_2$) and 1.42 (d, 6H, J=6.6 Hz, 2 CH$_3$). MS (FAB) 235 (M+1).

Part B: Va
(S,S)-N,N'-1,2-ethanediylbis[α-methyl-5-nitro-1, 3-dioxo-1H-benz[de]isoquinoline-2(3H)ethanethioamide]

A mixture of 3-nitro-1,8-naphthalic anhydride (1.98 g, 8.0 mmol), IVa (1.23 g, 4.0 mmol) and triethylamine (1.40 ml, 10 mmol) in 40 ml of ethanol was stirred at room temperature for 3 days and then heated to reflux overnight. The product was collected by filtration, and then purified by heating in 150 ml of ethanol to give 1.32 g (48.2%) of Va; mp 253°-254° C. (dec). $^1$H-NMR (DMSOd-d$_6$) δ 9.76 (broad, 2H, 2NH), 9.59 (d, 2H, J=2.2 Hz, aromatic protons), 8.96 (d, 2H, J=2.6 Hz, aromatic protons), 8.82 (d, 2H, J=7.6 Hz, aromatic protons), 8.67 (d, 2H, J=7.4 Hz, aromatic protons), 8.08 (t, 2H, J=7.7 Hz, aromatic protons), 5.72 (q, 2H, J=6.9 Hz, 2 CH), 3.79 (s, 4H, 2 CH$_2$) and 1.77 (d, 6H, J=6.6 Hz, 2 CH$_3$). MS (DCI) m/e 685 (M+1). HRMS M+684.1111 (calcd for $C_{32}H_{24}N_6O_8S_2$: 684.1097). $[\alpha]_D$ −30.62° (c=0.604, DMF).

EXAMPLE 7

By replacing t-BOC-alanine in Scheme I with t-BOC-β-alanine, Examples 7-9 can be prepared. N,N'-1,4-butanediylbis[5-nitro-1, 3-dioxo-1H-benz[de]isoquinoline-2(3H)-propanamide Light yellow solid (24% yield); mp 302°-303° C. (dec). $^1$H-NMR (TFA-d$_1$) δ 9.50 (d, 2H, J=1.6 Hz, aromatic protons), 9.42 (d, 2H, J=1.7 Hz, aromatic protons), 9.02 (d, 2H, J=7.3 Hz, aromatic protons), 8.72 (d, 2H, J=8.3 Hz, aromatic protons), 8.17(t, 2H, J=7.9 Hz, aromatic protons), 4.82 (t, 4H, J=5.7 Hz, 2 CH$_2$N), 3.69 (s, 4H, 2 CH$_2$N), 3.33 (t, 4H, J=5.1 Hz, 2 CH$_2$N) and 1.93 (s, 4H, 2 CH$_2$). MS (DCI) m/e 681 (M+1).

EXAMPLE 8

N,N'-1,3-propanediylbis[5-nitro-1,3-dioxo-1H-benz[de]isoquinoline-2(3H)-propanamide Light tan solid (80% yield); mp 300°-301.5° C. (dec). $^1$H-NMR (TFA-d$_1$) δ 9.45 (d, 2H, J=1.9 Hz, aromatic protons), 9.37 (d, 2H, J=1.7 Hz aromatic protons), 8.96 (d, 2H J=7.4 Hz, aromatic protons), 8.67 (d, 2H, J=8.3 Hz, aromatic protons), 8.11 (t, 2H, J=7.8 Hz, aromatic protons), 4.77 (t, 4H, J=6.5 Hz, 2 CH$_2$N), 3.68 (t, 2H, J=6.2 Hz, 2 CH$_2$N), 3.23 (t, 4H, J=6.0 Hz, 2 CH$_2$CO), and 2.12 (t, 2H, J=6.1 Hz, CH$_2$). MS (DCI) m/e 667 (M+1).

EXAMPLE 9

N,N'-1,2-ethanediylbis[5-nitro-1,3-dioxo-1H-benz[de]isoquinoline-2(3H)-propanamide Sand solid (20% yield); mp 321°-323° C. (dec). $^1$H-NMR (TFA-d$_1$) δ 9.42 (d, 2H, J=1.9 Hz, aromatic protons), 9.36 (d, 2H, aromatic protons), 8.94 (d, 2H, J=7.3 Hz, aromatic protons), 8.65 (d, 2H, J=2.2 Hz, aromatic protons), 8.10 (t, 2H, 7.9 Hz, aromatic protons), 4.77 (broad triplet, 4H, 2 CH$_2$N), 3.80 (s, 4H, 2 CH$_2$N) and 3.20 (broad triplet, 4H, 2 CH$_2$CO). MS (DCI) m/e 653 (M+1).

TABLE I

| EX. | X | Y | R$^1$, R$^4$ (stereo-conf.) | A | R$^2$ | R$^3$ | n | p |
|---|---|---|---|---|---|---|---|---|
| 1[a] | 3-NO$_2$ | H | CH$_3$(S) | O | H | H | 2 | 0 |
| 2[b] | 3-NO$_2$ | H | CH$_3$(R) | O | H | H | 2 | 0 |
| 3[c] | 3-NO$_2$ | H | (CH$_2$)$_2$SCH$_3$(S) | O | H | H | 3 | 0 |
| 4[d] | 3-NO$_2$ | H | CH$_3$(S) | O | H | H | 4 | 0 |
| 5[e] | 3-NO$_2$ | H | CH$_3$(S) | O | H | H | 3 | 0 |
| 6[f] | 3-NO$_2$ | H | CH$_3$(S) | S | H | H | 2 | 0 |
| 7[g] | 3-NO$_2$ | H | H | O | H | H | 4 | 1 |
| 8[h] | 3-NO$_2$ | H | H | O | H | H | 3 | 1 |
| 9[i] | 3-NO$_2$ | H | H | O | H | H | 2 | 1 |
| 10 | 3-NO$_2$ | H | H | O | H | H | 7 | 1 |
| 11 | 3-NO$_2$ | H | H | O | H | H | 8 | 1 |
| 12 | 3-NO$_2$ | H | H | O | H | H | 12 | 1 |
| 13 | 3-NO$_2$ | H | H | S | H | H | 2 | 1 |
| 14 | 3-NO$_2$ | H | H | S | H | H | 3 | 1 |
| 15 | 3-NO$_2$ | H | H | S | H | H | 4 | 1 |

Footnotes Table 1
[a] mp = 301-304° C.(d)
[b] mp = 293-294° C.(d)
[c] mp = 232-235° C.(d)
[d] mp = 285-288° C.(d)
[e] mp = 255-257° C.(d)
[f] mp = 253-254° C.(d)
[g] mp = 302-303° C.(d)
[h] mp = 300-301.5° C.(d)
[i] mp = 321-323° C.(d)

Tissue Culture

L1210 cells were maintained in RPMI=1640 a medium supplemented with 10% heat inactivated fetal bovine serum and 50 mL mercaptomethanol/liter medium (RPMI-L).

In vitro Growth Inhibitory Activity Determination

Exponential growing L1210 cells (1×10$^3$ cells) in 0.1 mL medium were seeded on day 0 in a 96-well microtiter plate. On day 1, 0.1 mL aliquot of medium containing graded concentration of test analogs was added to the initial volume. After incubation at 37° C. in a humidified incubator for 3 days, the plates were centrifuged briefly and 100 mL of the growth medium was removed. Cell cultures were incubated with 50 mL of 3-(4, 5-dimethylthiazol-2yl)-2,5- diphenyltetrazolium bromide (MTT; 1 mg/ml in Dulbecco's phosphate buffer saline) for 4 hours at 37° C. The resulting purple formazan precipitate was solubilized with 200 mL of 0.04 N HCl in isopropyl alcohol. Absorbance was read in a Titertek Multiskan MCC scaning well spectrophotometer (Flow Laboratories) at a test wavelength of 570 nm and a reference wavelength of 630 nm.

Data Analysis

The absorbances were stored on a floppy disk on a IBM-XT and uploaded on to a VAX computer. The $ID_{50}$ values were determined by a computer program that fit all of the data (8 determinations per concentration and 12 concentrations per test analog) to the following equation:

$$Y = ((AM - Ao)/(1 + (X/ID_{50})n)) + Ao$$

where
Am = absorbance of the control cells
Ao = absorbance of the cells in the presence of highest drug conc.
Y = observed absorbance
X = drug concentration
$ID_{50}$ = dose of drug that inhibits the growth of cells to one half that of the control cells.
Results are shown in Table II.

TABLE II

| Ex. No. | ID50 (ug/ml) |
|---------|--------------|
| 1 | 0.61 |
| 2 | 0.033 |
| 3 | 0.12 |
| 4 | 0.36 |
| 5 | 0.025 |
| 6 | 0.184 |
| 7 | 18.98 |
| 8 | >20.0 |
| 9 | 15.10 |

Dosage Forms

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals; either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of the recipient; nature and extent of symptoms; kind of concurrent treatment, frequency of treatment, and the effect desired. Usually a daily dosage of active ingredient can be about 5 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to make any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzaalkonium chloride, methyl- or propyl-paraben, and chlorbutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 100 milligrams of powdered active ingredient, 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose 11 milligrams of cornstrach and 98.8 milligrams of lactose. Appropriate coatings may be applied to increase palatability or delay.

Injectable

A parenteral composition suitable for administration b injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

What is claimed is:

1. A compound of the formula:

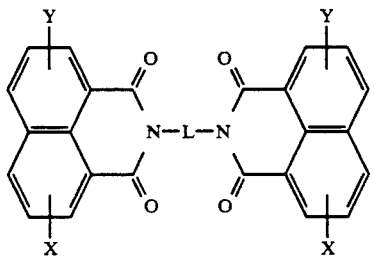

(i)

or a diastereomerically pure or racemate or a mixture of racemate and meso, pharmaceutically acceptable salts thereof, wherein:

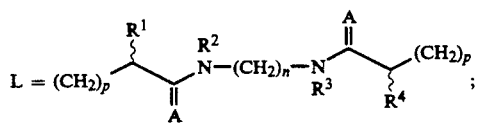

each $R^1$ and $R^4$ independently are H, $CH_3$ or $CH_2CH_3$;
$R^2$ and $R^3$ are H; each A independently is O or S;
XS and Y independently are H or $NO_2$,
each p is 0;
n is 2 or 3.

2. A compound of claim 1 wherein:
A is O; and
$R^1$ and $R^4$ are $CH_3$.

3. The compound of claim 1 which is (S,S)-N,N'-1,3-propanediylbis[α-methyl-5-nitro-1,3-dioxo-1H-benz-[de]isoquinoline-2(3H)-acetamide.

4. A pharmaceutical composition comprising a pharmaceutically acceptable carrier and a therapeutically effective amount of a compound of claim 1.

5. A pharmaceutical composition comprising a pharmaceutically acceptable carrier and a therapeutically effective amount of a compound of claim 2.

6. A pharmaceutical composition comprising a pharmaceutically acceptable carrier and a therapeutically effective amount of the compound of claim 3.

7. The compound of claim 1 which is (R,R)-N,N'-1,3-propanediylbis[α-methyl-5-nitro-1,3-dioxo-1H-benz-[de]isoquinoline-2(3H)-acetamide.

8. A pharmaceutical composition comprising a pharmaceutically acceptable carrier and a therapeutically effective amount of a compound of claim 7.

* * * * *